United States Patent
Liu et al.

(10) Patent No.: US 9,993,407 B2
(45) Date of Patent: *Jun. 12, 2018

(54) TEETH WHITENING METHODS, VISUALLY PERCEPTIBLE SIGNALS AND COMPOSITIONS THEREFOR

(71) Applicant: Colgate-Palmolive Company, New York, NY (US)

(72) Inventors: Zhiqiang Liu, Bridgewater, NJ (US); Long Pan, Cherry Hill, NJ (US); Shaotang Yuan, East Brunswick, NJ (US); Jairajh Mattai, Piscataway, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/411,144

(22) Filed: Jan. 20, 2017

(65) Prior Publication Data

US 2017/0128339 A1  May 11, 2017

Related U.S. Application Data

(63) Continuation of application No. 14/653,300, filed as application No. PCT/US2012/070534 on Dec. 19, 2012, now Pat. No. 9,572,756.

(51) Int. Cl.
*A61K 8/44* (2006.01)
*A61Q 11/00* (2006.01)
*A61K 8/02* (2006.01)
*A61K 8/27* (2006.01)

(52) U.S. Cl.
CPC .............. *A61K 8/44* (2013.01); *A61K 8/0216* (2013.01); *A61K 8/27* (2013.01); *A61Q 11/00* (2013.01); *A61K 2800/45* (2013.01); *A61K 2800/58* (2013.01)

(58) Field of Classification Search
CPC ............ A61K 2800/45; A61K 2800/58; A61K 8/0216; A61K 8/27; A61K 8/44; A61Q 11/00
See application file for complete search history.

(56) References Cited

U.S. PATENT DOCUMENTS

| | | | |
|---|---|---|---|
| 2,503,280 A | 4/1950 | Lockwood | |
| 2,507,088 A | 5/1950 | Bradley | |
| 2,527,686 A | 10/1950 | Sandberg | |
| 2,893,918 A | 7/1959 | Abramson | |
| 3,260,744 A | 7/1966 | Kenkichi | |
| 3,320,174 A | 5/1967 | Rubinfeld | |
| 3,372,188 A | 3/1968 | Terence | |
| 3,535,421 A | 10/1970 | Briner | |
| 3,538,230 A | 11/1970 | Morton | |
| 3,678,154 A | 7/1972 | Briner | |
| 3,741,911 A | 6/1973 | Shane | |
| 3,862,307 A | 1/1975 | Giulio | |
| 3,937,807 A | 2/1976 | Haefele | |
| 3,941,818 A | 3/1976 | Abdel-Moneni | |
| 3,959,458 A | 5/1976 | Agricola et al. | |
| 4,021,569 A * | 5/1977 | Abdel-Monem | .... A23K 20/142 514/494 |
| 4,051,234 A | 9/1977 | Gieske et al. | |
| 4,316,824 A | 2/1982 | Paneheri | |
| 4,339,432 A | 7/1982 | Ritchey et al. | |
| 4,340,583 A | 7/1982 | Wason | |
| 4,487,757 A | 12/1984 | Kiozpeoplou | |
| 4,565,693 A | 1/1986 | Marschner | |
| 4,599,152 A | 7/1986 | Ashmead | |
| 4,684,528 A | 8/1987 | Godfrey | |
| 4,687,663 A | 8/1987 | Schaeffer | |
| 4,842,847 A | 6/1989 | Amjad | |
| 4,866,161 A | 9/1989 | Sikes et al. | |
| 4,885,155 A | 12/1989 | Parran, Jr. et al. | |
| 5,004,597 A | 4/1991 | Majeti et al. | |
| 5,061,815 A | 10/1991 | Leu | |
| 5,156,845 A | 10/1992 | Grodberg | |
| 5,188,821 A | 2/1993 | Gaffar et al. | |
| 5,192,531 A | 3/1993 | Gaffar et al. | |
| 5,330,748 A | 7/1994 | Winston | |
| 5,504,055 A | 4/1996 | Hsu | |
| 5,643,559 A | 7/1997 | Eigen et al. | |
| 5,698,724 A | 12/1997 | Anderson et al. | |
| 5,707,679 A | 1/1998 | Nelson | |
| 5,714,447 A | 2/1998 | Jones et al. | |
| 5,911,978 A | 6/1999 | Carr et al. | |

(Continued)

FOREIGN PATENT DOCUMENTS

| | | |
|---|---|---|
| CN | 101606639 | 12/2009 |
| CN | 102811698 | 12/2012 |

(Continued)

OTHER PUBLICATIONS

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf. Retrieved Sep. 26, 2013.

Chemical compound [online] retrieved on May 23, 2016 from: http://www.thefreedictionary.com/chemical+compound; 3 pages.

Cold Cure ([online] retrieved from: http://coldcure.com/html/fraction.html on Jan. 29, 2016, 2011:3 pages).

Complex [online] retrieved on May 23, 2016 from: http://www.chemicool.com/definition/complex.html; 3 pages.

Deschaume et al., "Interactions of aluminum hydrolytic species with biomolecules," New Journal of Chemistry, 2008, 32:1346-1353.

(Continued)

*Primary Examiner* — Ernst V Arnold

(57) ABSTRACT

Described herein are methods of cleaning a tooth comprising administering a composition comprising a zinc amino acid halide complex to the oral cavity; and retaining the composition in the oral cavity for a time sufficient to form a precipitate.

15 Claims, No Drawings

(56) References Cited

U.S. PATENT DOCUMENTS

| | | |
|---|---|---|
| 5,993,784 A | 11/1999 | Hill |
| 6,121,315 A | 9/2000 | Nair et al. |
| 6,156,293 A | 12/2000 | Jutila et al. |
| 6,607,711 B2 | 8/2003 | Pedersen |
| 6,685,920 B2 | 2/2004 | Baig et al. |
| 6,969,510 B2 | 11/2005 | Holerca et al. |
| 8,067,627 B2 | 11/2011 | Newsome et al. |
| 8,247,398 B2 | 8/2012 | Goel |
| 2004/0042978 A1 | 3/2004 | Embro |
| 2004/0122088 A1 | 6/2004 | Newsome et al. |
| 2004/0033916 A1 | 10/2004 | Holerca et al. |
| 2004/0198998 A1 | 10/2004 | Holerca et al. |
| 2006/0024252 A1 | 2/2006 | Esposito et al. |
| 2007/0071698 A1 | 3/2007 | Doss |
| 2009/0202454 A1 | 8/2009 | Prencipe |
| 2009/0220444 A1 | 9/2009 | Teckenbrock et al. |
| 2010/0021573 A1 | 1/2010 | Gonzalez et al. |
| 2010/0266480 A1 | 10/2010 | Huang |
| 2010/0330163 A1 | 12/2010 | Soparkar |
| 2011/0076309 A1 | 3/2011 | Misner et al. |
| 2011/0229536 A1 | 9/2011 | Kvitnitsky et al. |
| 2013/0017240 A1 | 1/2013 | Porter et al. |
| 2014/0170086 A1 | 6/2014 | Pan et al. |

FOREIGN PATENT DOCUMENTS

| | | |
|---|---|---|
| CN | 103156073 | 6/2013 |
| CN | 103535536 | 1/2014 |
| DE | 735096 | 5/1943 |
| EP | 2052978 | 2/1981 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2109685 | 6/1983 |
| GB | 2243775 | 11/1991 |
| JP | S57-158724 | 9/1982 |
| JP | 2004175790 | 6/2004 |
| JP | 2009084201 | 4/2009 |
| JP | 2010132639 | 6/2010 |
| WO | WO86/00004 | 1/1986 |
| WO | WO9917735 | 4/1999 |
| WO | WO199917735 | 4/1999 |
| WO | WO0169087 | 9/2001 |
| WO | WO2004054531 | 7/2004 |
| WO | WO2004/064536 | 8/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098814 | 6/2012 |
| WO | WO2014/098813 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |
| WO | WO2014204439 | 12/2014 |

OTHER PUBLICATIONS

Dirkse, T.P., Zinc Oxide and Hydroxide, NIST Critical Evaluation, 1984, downloaded from http://srdata.nist.gov/solubility/IUPAC/SDS-23/SDS-23-pages_156.pdf (last accessed Aug. 26, 2016).

European Food Safety Authority, "Scientific Opinion on the safety and efficacy of tetra-basic zinc chloride for all animal species," EFSA Journal, 2012, 10(5):2672.

Fundamentals of Inorganic Chemistry 2ed 2012: 2 pages.

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 dated Oct. 22, 2013.

International Search Report and Written Opinion for International Application No. PCT/US2012/070492 dated Oct. 22, 2013.

International Search Report and Written Opinion for International Application No. PCT/US2012/070498 dated Sep. 4, 2013.

International Search Report and Written Opinion for International Application No. PCT/US2012/070501 dated Oct. 21, 2013.

International Search Report and Written Opinion for International Application No. PCT/US2012/070505 dated Nov. 20, 2013.

International Search Report and Written Opinion for International Application No. PCT/US2012/070506 dated Oct. 14, 2013.

International Search Report and Written Opinion for International Application No. PCT/US2012/070513 dated Oct. 14, 2013.

International Search Report and Written Opinion for International Application No. PCT/US2012/070521 dated Sep. 30, 2013.

International Search Report and Written Opinion for International Application No. PCT/US2012/070525 dated Sep. 27, 2013.

International Search Report and Written Opinion for International Application No. PCT/US2012/070528 dated Sep. 30, 2013.

International Search Report and Written Opinion for International Application No. PCT/US2012/070534 dated Sep. 26, 2013.

International Search Report and Written Opinion for International Application No. PCT/US2012/070537 dated Oct. 11, 2013.

International Search Report and Written Opinion for International Application No. PCT/US2013/046268 dated Apr. 22, 2014.

International Search Report and Written Opinion for International Application No. PCT/US2013/050845 dated Aug. 13, 2014.

International Search Report and Written Opinion for International Application No. PCT/US2013/068852 dated Nov. 10, 2014.

International Search Report and Written Opinion for International Application No. PCT/US2013/068854 dated Oct. 20, 2014.

International Search Report and Written Opinion for International Application No. PCT/US2013/068859 dated Aug. 4, 2014.

International Search Report and Written Opinion for International Application No. PCT/US2013/068860 dated Oct. 22, 2014.

International Search Report and Written Opinion for International Application No. PCT/US2013/070932 dated Jul. 24, 2014.

International Search Report and Written Opinion for International Application No. PCT/US2014/042947 dated Aug. 22, 2014.

International Search Report and Written Opinion for International Application No. PCT/US2014/042948 dated Aug. 26, 2014.

International Search Report and Written Opinion for International Application No. PCT/US2014/043051 dated Feb. 18, 2015.

Kondrot, "The Importance of Zinc," http://www.healingtheeye.com/Articles/zinc.html, Feb. 21, 2012.

Kuriakose et al. (Bellstein J. Nanotechol. 2013(4):763-770).

Liang et al., "In vitro scratch assay: a convenient and inexpensive method for analysis of cell migration in vitro," Nature Protocols, 2007, 2(2):329-333.

Liu et al., "The research on zinc coordination number 5 odd structure in zinc complex with L-lysine," J. Molecular Science, 2000, 16(2):114-117, abstract only in English.

Lu et al., "Albumin as a zinc carrier: properties of its high-affinity zinc-binding site". Biochem. Soc. Trans., 2008, 36:1317-1321.

(56) References Cited

OTHER PUBLICATIONS

Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:6555-63.
Pashley et al. Dentin permeability effects of desensitizing dentifrices in vitro, J Periodontol, 1984;55(9):522-525.
Prasad, "Zinc:role in immunity, oxidative stress and chronic inflammation,"Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Walfingite, c-Zn(OH)2, and simonkolleite, Zn5(OH)8Cl2•H2O, two new minerals from Richelsdorf Hesse, F.R.G.," N. Jb. Miner. Mh., Apr. 1985, pp. 145-154.
Seil et al., "Antibacterial effect of zinc oxide nanoparticles combined with trasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Toxicological Profile for Zinc1994 p. 125; 1 page.
Twetman et al., 2003, "Caries-preventative effect of fluoride toothpaste a systematic review, " Acta Odontol Scand., Dec. 2003, 61(6)347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions,"J. of Materials Chemistry, 2011, 21;19005-19012.
Yousef et al., "In vitro antibacterial activity and minimum inhibitory concentration of zinc oxide and nano-particle zinc oxide against pathogenic strains," J. of Health Sciences, 2012, 2(4);38-42.
Zhu et al., "Synthesis and Crystal Structure of [Zn±{H2N(CH2)4CH(NH2)COONa}2SO4−]•H20,", Chinese Science Bulletin, Sep. 1990, 35(18):1521-1525.

* cited by examiner

TEETH WHITENING METHODS, VISUALLY PERCEPTIBLE SIGNALS AND COMPOSITIONS THEREFOR

CROSS-REFERENCE TO RELATED APPLICATIONS

This application is a continuation of U.S. application Ser. No. 14/653,300, filed Jun. 18, 2015, which is a U.S. national stage application under 35 U.S.C. § 371 of International Application No. PCT/US2012/070534, filed Dec. 19, 2012, the entireties of which are incorporated herein by reference.

BACKGROUND

There is a need for oral care products to whiten teeth. Bleaching materials such as peroxide are commonly used to whiten teeth, but peroxide is difficult to formulate and deliver in sufficient concentrations to provide a good whitening effect. White pigments such as zinc oxide are also used, but such insoluble pigments are also difficult to formulate and deliver.

There is also a need for improved, consumer-friendly products and methods to encourage users to brush their teeth for a longer period of time. It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth. Toothpaste comprising colored film fragments or encapsulates that release pigment upon adequate brushing are known, but these pigments provide no particular benefit to the teeth.

SUMMARY

It is surprisingly discovered that while zinc amino acid halide complexes are soluble, colorless and stable in concentrated aqueous solution, even at neutral pH, the zinc amino acid halide complex decomposes in more dilute solution, to provide a relatively insoluble zinc-containing precipitate, e.g. a zinc oxide precipitate. This dynamic is surprising because one would expect an ionic complex to remain in solution as the solution becomes more dilute. This precipitation can usefully signal that a minimum brushing period has elapsed, and moreover the precipitation provides controlled deposition of the white zinc-containing precipitate on the teeth.

The invention thus provides in one embodiment a method for (i) indicating an amount of time for brushing the teeth and/or (ii) whitening the teeth, comprising brushing the teeth with a dentifrice comprising a zinc amino acid halide complex, in the presence of water, until the zinc amino acid halide complex provides a zinc precipitate from the dentifrice and water. The method comprises brushing with a dentifrice that contains a zinc amino acid halide complex until the zinc amino acid halide complex decomposes to provide a white zinc-containing precipitate. The time can be, for example, 30 to 120 seconds, for example 45-60 seconds for a child or 90-120 seconds for an adult.

For example, in one embodiment, the dentifrice is a clear gel. After a period of brushing, e.g., at least 30 seconds, the zinc amino acid halide complex is disrupted, and the clear gel toothpaste is suddenly rendered white and opaque by the precipitate, signaling to the user that he or she has brushed for an adequate period.

In one particular embodiment, the zinc-amino acid complex is a zinc-lysine-chloride complex, for example the novel complex designated which may be formed from a mixture of zinc oxide and lysine hydrochloride. ZLC has the chemical structure $[Zn(C_6H_{14}N_2O_2)_2Cl]^+ Cl^-$, and may exist in solution of the cationic cation $([Zn(C_6H_{14}N_2O_2)_2Cl]^+)$ and the chloride anion, or may be a solid salt, e.g., a crystal, optionally in mono- or dihydrate form.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention thus provides in particular embodiments a method of cleaning and/or whitening the teeth (Method 1) comprising brushing with a dentifrice comprising a zinc-amino acid-halide complex in the presence of water, until the complex disintegrates, wherein the white precipitate thus formed provides a signal to the user of adequate brushing, and/or provides a whitening benefit to the teeth, e.g., 1.1. Method 1 wherein the brushing time before the complex disintegrates is between 30 and 180 seconds, e.g., about 45-60 seconds for a toothpaste for use by a child and about 90-120 seconds for a toothpaste for use by an adult.
1.2. Method 1 wherein the amino acid in the complex is selected from lysine and arginine, in free or orally acceptable acid addition salt form, e.g., hydrochloride form.
1.3. Any of the foregoing methods wherein the halide in the complex is selected from chloride, fluoride, bromide and mixtures thereof, e.g. chloride.
1.4. Any of the foregoing methods wherein in the complex the molar ratio of Zn:amino acid is from 3:1 to 1:5, e.g., about 1:2 and the molar ratio of Zn:halide is from 3:1 to 1:3, e.g., about 1:2.
1.5. Any of the foregoing methods, wherein zinc is present in an amount of 0.05 to 10% by weight of the dentifrice, optionally at least 0.1, at least 0.2, at least 0.3, at least 0.4, at least 0.5, at least 1, at least 2, at least 3, or at least 4 up to 10% by weight of the dentifrice, e.g. about 1-3%, e.g., about 2-2.7% by weight.
1.6. Any of the foregoing methods, wherein amino acid is present in an amount of 0.05 to 30% by weight of the dentifrice, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.
1.7. Any of the foregoing methods, wherein the dentifrice comprises a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3
1.8. Any of the foregoing methods wherein the zinc amino acid complex is a zinc lysine chloride complex (e.g., $(ZnLys_2Cl)^+Cl^-$ or $(ZnLys_3)^{2+}Cl_2$) or a zinc arginine chloride complex.
1.9. Any of the foregoing methods, wherein the zinc amino acid complex is a zinc lysine chloride complex, e.g., ZLC, e.g., a zinc lysine chloride complex having the chemical structure $[Zn(C_6H_{14}N_2O_2)_2Cl]^+$ $Cl^-$, either in solution of the cationic cation (e.g., $[Zn(C_6H_{14}N_2)_2Cl]^+$) and the chloride anion, or in solid salt form, e.g., crystal form, optionally in mono- or dihydrate form.

1.10. Any of the foregoing methods wherein the dentifrice is in the form of a clear gel which provides a zinc oxide precipitate when diluted.

1.11. Any of the foregoing methods wherein the zinc-amino acid-halide complex is present in the dentifrice an effective amount, e.g., in an amount corresponding to 0.1-3% by weight of zinc, e.g., about 0.2-1% by weight of zinc in the dentifrice.

1.12. Any of the foregoing methods additionally providing an oral care benefit selected from reducing and inhibiting acid erosion of the enamel, cleaning the teeth, reducing bacterially-generated biofilm and plaque, reducing gingivitis, inhibiting tooth decay and formation of cavities, and/or reducing dentinal hypersensitivity.

1.13. Any of the foregoing methods wherein the dentifrice is in the form of a clear gel, wherein the zinc-amino acid-halide complex is a zinc-lysine-chloride complex having the chemical structure $[Zn(C_6H_{14}N_2O_2)_2Cl]^+$ $Cl^-$ present in an amount corresponding to 0.1-2%, e.g., about 0.5% zinc by weight of the dentifrice, and further comprising humectant, e.g., sorbitol, propylene glycol and mixtures thereof, e.g., in an amount of 45-65%, e.g., about 50-60%, thickeners, e.g., cellulose derivatives, e.g., selected from carboxymethyl cellulose (CMC), trimethyl cellulose (TMC) and mixtures thereof, e.g., in an amount of 0.1-2%, sweetener and/or flavorings, and water, e.g., wherein the dentifrice is an oral gel comprising:

| Ingredients | % |
|---|---|
| Sorbitol | 40-60%, e.g., 50-55% |
| ZLC | to provide 0.1-2% Zn, e.g about 0.5% Zn |
| Carboxymethyl cellulose (CMC) and Trimethyl cellulose (TMC) | 0.5-1%, e.g., about 0.7% |
| Flavoring and/or sweetener | 0.01-1% |
| Propylene Glycol | 1-5%, e.g., about 3.00% |

The invention also provides the use of a zinc amino acid halide complex in a method according to any of the foregoing Methods 1, et seq. or in the manufacture of a dentifrice for use in any of the foregoing Methods 1, et seq.

The combination of zinc, amino acid, and halide in an aqueous media forms a cationic complex-halide salt. The zinc amino acid halide is a water soluble complex formed from the halide acid addition salt of zinc (e.g., zinc chloride) and an amino acid, or from the halide acid addition salt of an amino acid (e.g., lysine hydrochloride) and zinc ion source, e.g., zinc oxide or TBZC, and/or from combination of all three of a halogen acid, an amino acid, and a zinc ion source.

The zinc ion source for combination with an amino acid hydrohalide or an amino acid plus halogen acid may be any source that provides $Zn^{++}$ ions efficiently, for example zinc oxide, zinc chloride, tetrabasic zinc chloride, zinc carbonate, zinc nitrate, zinc citrate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2 \cdot H_2O$, also referred to as basic zinc chloride, zinc hydroxychloride, or zinc oxychloride. It is a colorless crystalline solid insoluble in water. Both of these materials are found to be soluble in water in the presence of an amino acid and provide, a source of zinc ions while restricting the available anions, as an excess of anions can interfere with the complex formation.

The amino acid source can be any amino acid. Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid.

In some embodiments, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine, in other embodiments, the amino acid is arginine. Neutral amino acids, such as glycine, and even acidic amino acids, such as aspartic acid, however, are also capable of forming salts with strong acids, such as halogen acids. In some embodiments the amino acid is a neutral or acidic amino acid, e.g., glycine.

The halide source can be part of the zinc source, such as zinc chloride or tetrabasic zinc chloride. The halide source can be part of the amino acid, such as an amino acid hydrohalide. Also, the halide source can be a halogen acid. The halide may be chloride, bromide, or iodide, most typically chloride. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

In certain embodiments, the amount of zinc amino acid halide in the composition for use in the above-described methods is 0.05 to 40% by weight of the composition. In certain embodiments, precursors, e.g., zinc oxide and amino acid hydrohalide, are present in amounts such that when combined into the zinc amino acid halide, the zinc amino acid halide would be present in an amount of 0.05 to 40% by weight of the composition. In either of these embodiments, the amount of the zinc amino acid halide can be varied for the desired purpose, such as an antibacterial agent or as an antiperspirant. In other embodiments, the zinc amino acid halide is present in an amount of 0.05 to 40% by weight of the composition, optionally at least 0.1, at least 0.2, at least 0.3, at least 0.4, at least 0.5, at least 1, at least 2, at least 3, or at least 4 up to 40% by weight of the composition, or, optionally, 0.1 up to 30%, up to 20%, up to 10%, up to 5%, up to 4%, up to 3%, up to 2%, or up to 1% by weight of the composition.

When the zinc amino acid halide is formed from precursor materials, the precursor materials are preferably used in molar ratios approximately as required to produce the desired zinc amino acid halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid. For example, in one embodiment to produce zinc lysine chloride (ZnLys$_3$Cl$_2$), the molar ratios of the elements in the precursor materials would include about 1 molar equivalent Zn$^{2+}$:3 molar equivalents Lys:2 molar equivalents Cl$^-$.

In some embodiments, the total amount of zinc in the dentifrice for use in the invention is 0.05 to 3% by weight of the dentifrice. In other embodiments, the total amount of zinc is at least 0.1, at least 0.2, at least 0.3, at least 0.4, at least 0.5, or at least 1 up to 2.5 or 3% by weight of the dentifrice. In other embodiments, the total amount of zinc in the dentifrice is less than 5, less than 4, less than 3, less than 2, or less than 1 to 0.05% by weight of the composition.

In certain embodiments, a molar ratio of zinc to amino acid in the dentifrice for use in the methods of the invention is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the zinc amino acid halide is a zinc-lysine complex having the formula [Zn(C$_6$H$_{14}$N$_2$O$_2$)$_2$Cl]$^+$Cl$^-$ (sometimes referred to herein as "ZLC").

In certain embodiments, the zinc amino acid halide has the formula ZnAA$_3$Hal$_2$, wherein Zn is a divalent zinc ion, AA is an amino acid residue, and Hal is a halide ion.

Some embodiments of the present invention provide methods of cleaning a tooth comprising: administering a composition comprising a zinc amino acid halide complex to the oral cavity; and retaining the composition in the oral cavity for a time sufficient to form a precipitate. In some embodiments, the precipitate provides a signal to the user. In some embodiments, the signal is a visually perceivable signal. In some embodiments, the signal indicates that the composition has been used for the appropriate time.

In some embodiments, the composition forms a precipitate after 30 seconds in the oral cavity. In some embodiments, the composition forms a precipitate after 90 seconds in the oral cavity. In some embodiments, the composition forms a precipitate after 120 seconds in the oral cavity.

The compositions and formulations for use with the methods herein are described with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

The general reaction for formation of ZLC is as follows:

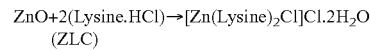
(ZLC)

A 2:1 molar ratio of ZnO:Lysine.HCl suspension is prepared with stirring at room temperature for about 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. The key parameters for this structure is: Crystal system: Monoclinic, Space group: P 21. Unit cell dimensions: a=5.2751(8) Å, b=17.055(3) Å, c=11.4072(18) Å. α=90°, β=94.064(2)°, γ=90°. In this complex, Zn cation is coordinated by two lysine ligands with two N atoms from NH$_2$ groups and O atoms from carboxylic groups in an equatorial plane. It displays a distorted square-pyramidal geometry with the apical position occupied by a Cl atom. This novel structure gives rise to a positive cation moiety, to which a Cl anion is combined to form an ionic salt.

Laboratory Scale-Up Synthesis of Pure ZLC Powder:

2 mole of LysineHCl is dissolved in 1000 ml DI water with stirring at room temperature, 1 mole of solid ZnO is added slowly to the LysineHCl solution with stirring and the stirring is continued at RT overnight (about 12 hours). The suspension solution is centrifuged at high speed for 15 mins. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained. PXRD confirms the purity of ZLC powder compared to ZLC crystal.

Example 2

An oral gel toothpaste with ZLC as active ingredient is formulated and compared to other formulations containing ZnCl$_2$, ZnO, and NaF. Only the ZLC formulation shows competitive clarity as current gel phase containing NaF. The precipitation property of ZLC gel phase is also investigated by hydrolysis reaction study, providing evidence that when the teeth are being brushed with toothpaste containing ZLC actives, the insoluble particles formed during brushing can penetrate into the dentin tubules and block the tubules resulting to anti-sensitive effect and signal for the consumer.

Four 500.0 g gel phase batches which contain NaF (control), ZLC, ZnCl$_2$ and ZnO as active ingredient are formulated with the ingredients shown in Table 8. The clarity of samples with different actives is compared, and the precipitation characteristic of ZLC gel phase by dilution is evaluated. The concentration of zinc ions in ZLC solution is 25300 ppm obtained by ICP, which in terms gives approximately 17% weight of ZLC actives in the solution. Zinc ion concentration in the following batches are all prepared at 0.5% (w/w) zinc level.

TABLE 1

| Ingredients | % | Loading (g) | Actual (g) |
|---|---|---|---|
| Oral gel with ZLC (2.53% Zn) | | | |
| Sorbitol 70% sol | 76.03 | 380.15 | 380.14 |
| ZLC aqueous solution 2.53% Zn | 20 | 100 | 100 |
| Carboxymethyl cellulose (CMC) and Trimethyl cellulose (TMC) | 0.70 | 3.5 | 3.51 |
| Na Saccharin | 0.27 | 1.35 | 1.35 |
| Propylene Glycol | 3 | 15 | 15 |
| Total | 100 | 500 | 500 |
| % Zn | | 0.506 | 0.5060% |
| Oral gel with $ZnCl_2$ (47.97% Zn) | | | |
| Sorbitol 70% sol | 80 | 400 | 399.99 |
| ZnCl2 47.97% Zn | 1.06 | 5.275 | 5.27 |
| CMC TMC | 0.7 | 3.5 | 3.5 |
| Na Saccharin | 0.27 | 1.35 | 1.35 |
| Propylene Glycol | 3 | 15 | 14.98 |
| DI water | 14.98 | 74.875 | 74.91 |
| Total | 100 | 500 | 500 |
| % Zn | | 0.508 | 0.5056% |
| Oral gel with ZnO (80.34% Zn) | | | |
| Sorbitol 70% sol | 80.2 | 401 | 400.99 |
| ZnO 80.34% Zn | 0.63 | 3.15 | 3.15 |
| CMC TMC | 0.7 | 3.5 | 3.5 |
| Na Saccharin | 0.27 | 1.35 | 1.35 |
| Propylene Glycol | 3 | 15 | 15 |
| DI water | 15.2 | 76 | 75.99 |
| Total | 100 | 500 | 499.98 |
| % Zn | | 0.505 | 0.5062% |
| Oral gel with NaF | | | |
| Sorbitol 70% sol | 80.20 | 401 | 401 |
| NaF | 0.76 | 3.8 | 3.79 |
| CMC TMC | 0.7 | 3.5 | 3.51 |
| Na Saccharin | 0.27 | 1.35 | 1.35 |
| Propylene Glycol | 3 | 15 | 15.01 |
| DI water | 15.07 | 75.35 | 75.36 |
| Total | 100 | 500 | 500.02 |

Lambda 25 UV/VIS Spectrometer (PerkinElmer) is used to obtain absorbance information for all samples in order to compare the clarity of gel phase between different actives. Absorbance is a logarithmic measure of the amount of light that is absorbed when passing through a substance. Since the particles in the gel absorb light, the more particles existing in solution, the more light absorbed by the gel. Thus, a small number a absorbance of a gel indicates a higher clarity. The absorbance is corrected by using deionized (DI) water as the blank solution under the light source wavelength of 610 nm. ZnO is not dissolved and is suspended in gel phase resulting a high absorbance. Even though. $ZnCl_2$ is soluble in water, the gel phase containing $ZnCl_2$ appears cloudy. Only the gel phase formulated by ZLC forms a homogenous solution and shows competitive clarity as the gel phase formulated by NaF. The absorbance and pH of all samples are shown in Table 2.

TABLE 2

| | NaF | ZLC | $ZnCl_2$ | ZnO |
|---|---|---|---|---|
| Absorbance | 0.0344 | 0.1765 | 0.9204 | 2.4626 |
| pH | 7.63 | 7.37 | 5.25 | 8.30 |

Dilution Experiment:
All original gel phase batch are diluted into 2 fold, 4 fold, 8 fold, 16 fold and 32 fold. There is a decrease of absorbance as the $ZnCl_2$ gel and ZnO gel are further diluted, and an increase of absorbance in the further diluted ZLC gel solution. This observation confirms the formation of precipitate when ZLC gel is being diluted by water. The pHs of 2 fold, 4 fold, 8 fold, 16 fold, and 32 fold diluted ZLC gel solution are 7.71, 7.91, 8.03, 8.12, and 8.14, respectively.

TABLE 3

| Active Ingredient | 2 fold dilution | 4 fold dilution | 8 fold dilution | 16 fold dilution | 32 fold dilution |
|---|---|---|---|---|---|
| NaF | 0.0106 | 0.0104 | 0.0107 | 0.0075 | 0.0137 |
| ZLC | 0.1436 | 0.1887 | 0.1860 | 0.1336 | 0.2998 |
| $ZnCl_2$ | 0.7315 | 0.3700 | 0.1701 | 0.0570 | 0.0280 |
| ZnO | 2.4630 | 2.5340 | 2.1883 | 1.8638 | 1.0492 |

The above gels can be used alone preferred where the objective is to provide a signal to the user of adequate brushing time) or in a toothpaste having a gel phase and an abrasive paste phase. ZLC as active ingredient in gel phase of toothpaste formulation. Compared with the gel phase batches formulated by $ZnCl_2$ and ZnO, only the formulation with ZLC as active shows competitive clarity and pH as the one used in commercial product (NaF as active ingredient). The dilution experiment shows that only ZLC gel phase can form insoluble precipitate from transparent gel when it is diluted. The formation of insoluble precipitate by dilution facilitates the formation of "plugs" in dentine tubules after using this type of toothpaste, it whitens the teeth, and it provides a white precipitate signal during consumer use.

Example 3

Various dilutions of ZLC are prepared to evaluate its efficiency in producing visible precipitates and/or flocculation, which can be delivered onto a dental surface (dentine and/or enamel) for whitening benefits.

A neat solution of ZLC is prepared by 1), reacting 0.5 mole of ZnO powder with 1 mole of lysine HCl in 1 liter of water at room temperature for about 2 hours, and 2) collecting the supernatant through centrifugation followed by filtration using a 0.45 micron membrane. The neat solution has a zinc concentration of 2.39% by weight, and a pH of about 7.03.

Dilution experiment is conducted by mixing the neat solution with deionized water. The neat solution is diluted by 2×, 4×, 6×, 7×, 8×, 10×, 12×, 16×, 20×, 24×, 28×, and 32×, corresponding to initial zinc concentrations of 1.20%, 0.598%, 0.398%, 0.341%, 0.299%, 0.239%, 0.199%, 0149%, 0120%, 0.0996%, 0.0854%, 0.0747%, by weight, respectively. The diluted samples are kept at 37° C., and the rates at which flocculation/precipitation occurred are monitored. Dilutions with initial zinc concentrations at 0.149% and 0.199% are able to generate some visible flocculation within 30 minutes from the time point when the stock solution is mixed with water. One hour from mixing, visible flocculation are observed in dilutions with initial zinc concentrations of between 0.0854% and 0.239%. One and a half hours after mixing, visible flocculation are observed in dilutions with initial zinc concentrations of between 0.0747% and 0.239%. Two hours after mixing, the additional sample with initial zinc concentration of 0.299% also showed presence of flocculation. After a total of 19 hours, flocculation and/or precipitation can be observed in all samples except the one with initial zinc concentration of 1.20%, and the ones with initial zinc concentrations of between 0.0747% and 0.239% exhibit the most precipitates.

pH values of final diluted samples are suitable for oral care applications. The samples with initial zinc concentrations of 0.0747%, 0.0854%, 0.0996%, 0.120%, 0149%, 0.199 wt % and 0.239%, had a final pH value of 7.99, 8.13, 8.11, 7.97, 7.99, 6.80, and 6.70, respectively. These pH values are well within the range of 5.5 to 10, which defines the suitable range far oral care formulations.

Zinc is present in the precipitates primarily in the form of zinc oxide. Lysine is present in the precipitate as an integral component thereof and/or as an impurity.

Example 4

Confocal images demonstrate the efficiency of ZLC in generating deposits on dentine surface, under conditions where visible precipitation can be formed. The deposits impart a white color to the dentine surface upon examination by the naked eyes.

The deposition/occlusion assay is conducted using human dentine slices and the neat solution of Example 3. The dentine slices are prepared by cutting human tooth into thin dentine sections of about 800 microns in thickness, designating a test side, sanding said test side using a sandpaper of about 600 grit, polishing said test side using, a Buehler polishing cloth and 5 micron Buehler aluminum oxide, acid-etching said dentine section in 1% (by weight) citric acid solution for about 20 seconds, sonicating said dentine section for 10 minutes, and storing said dentine section in phosphate buffered saline (PBS, pH 7.4, Gibco Cat. No, 10010).

For treatment, the neat solution is diluted 16-fold with water, yielding a treatment solution with initial zinc concentration of about 0.149% by weight. The dentine section is immersed in the treatment solution for 1 hour at 37° C. The treated dentine section is then removed from the treatment solution, and rinsed 4 times, each time with 1 mL of PBS. The dentine section is then dried using a paper-based tissue and examined under confocal microscope in both XYZ and XYZ modes. Subsequent treatments are conducted in the same manner.

Progressive deposition and occlusion can be observed via confocal imaging. The first treatment leads to noticeable deposition. The second treatment leads to complete surface coverage, including blocking of substantially all tubule openings. The surface deposits can be 10 microns or more in thickness. After the third treatment, complete surface coverage and complete blocking of tubule openings are observed. The surface deposits can be 25 microns or more in thickness.

Example 5

Confocal images demonstrate the efficiency of ZLC in generating deposit on dentine surface, under conditions where visible precipitation is not observed.

A new dentine sections, as prepared following the procedure in Example 4, is repeatedly treated with ZLC dilutions with initial zinc concentration of 0.0747% by weight. Each treatment involved 32 mL of diluted solution (1 mL of neat solution from Example 3 and 31 mL of deionized water) and lasts for 10 minutes at 37° C., during which time, no precipitation is observed by naked eyes. The dentine section is examined under the confocal microscope after each treatment. After 4 consecutive treatments, significant surface deposition is observed. After 12 consecutive treatments, complete surface coverage is observed leaving no sign of presence of tubule openings.

Therefore, surface deposition can occur under conditions, both in terms of dilution ratios and treatment durations that do not produce visible precipitation. As a result, the whitening benefits can be achieved under wider ranges of dilution ratios and shorter treatment times than what can be directly inferred from Examples 3 and 4.

Example 6

Spectrophotometric analysis proves the whitening efficacy of the ZLC treatment. After the third treatment, the dentine section of Example 4 is dried and examined under a Spectroshade™ spectrophotometer (Handy Dental Type 71,3000). The treated dentinal area is included and the enamel rim is excluded from the examination and subsequent data processing. The CIELAB color reading is $L^*=86.6$, $a^*=-1.7$, and $b^*=1.5$. A similarly prepared dentine section without treatment yielded a reading of $L^*=72.5$, $a^*=-1.9$, and $b^*=10.3$. It is commonly understood that, by definition, $L^*=0$ means black and $L^*=100$ indicates diffuse white, negative $a^*$ value indicates green while positive values indicate magenta, and negative $b^*$ values indicate blue and positive values indicate yellow. It can be concluded that ZLC treatment enhanced the overall whiteness and reduced the yellowness of the dentine surface.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A method of cleaning a tooth comprising:
   administering a composition comprising a zinc amino acid halide complex in an amount of 0.1 to 5% by weight of the composition, to the oral cavity; and
   retaining the composition in the oral cavity for a time sufficient to form a precipitate;
   wherein the zinc-amino acid-halide complex is a complex having the formula $[Zn(Lysine)_3]^{2+}Cl_2^{2-}$; and
   wherein the composition is in the form of a clear gel which provides a zinc oxide precipitate when diluted.

2. The method of claim 1, wherein the precipitate provides a signal to the user.

3. The method of claim 2, wherein the signal is a visually perceivable signal.

4. The method of claim 2 wherein the signal indicates that the composition has been used for the appropriate time.

5. The method of claim 1, wherein the composition is diluted to an extent sufficient to form a precipitate after 30 seconds in the oral cavity.

6. The method of claim 1, wherein the composition is diluted to an extent sufficient to form a precipitate after 90 seconds in the oral cavity.

7. The method of claim 1, wherein the composition is diluted to an extent sufficient to form a precipitate after 120 seconds in the oral cavity.

8. The method of claim 1, wherein the precipitate is a white precipitate and wherein the precipitate provides a whitening benefit to the teeth.

9. The method of claim 1, wherein the complex is formed from precursors comprising a zinc source, a lysine source and a chloride source.

10. The method of claim 9, wherein the precursors are present in the composition at a ratio to provide about 1 molar equivalent of zinc to about 3 molar equivalents of lysine to about 2 molar equivalents of chloride.

11. The method of claim 9, wherein the zinc source is zinc chloride, tetrabasic zinc chloride or zinc oxide, and wherein the amino acid source is lysine or lysine hydrochloride.

12. The method of claim 1 additionally providing an oral care benefit selected from reducing and inhibiting acid erosion of the enamel, cleaning the teeth, reducing bacterially-generated biofilm and plaque, reducing gingivitis, inhibiting tooth decay and formation of cavities, and/or reducing dentinal hypersensitivity.

13. The method of claim 1 which is a method for whitening the teeth.

14. The method of claim 1 which is a method for cleaning the teeth for a particular period.

15. The method of claim 11, wherein the zinc source is tetrabasic zinc chloride and the amino acid source is lysine hydrochloride.

\* \* \* \* \*